United States Patent
Tran (10) Patent No.: US 8,753,301 B2
(45) Date of Patent: Jun. 17, 2014

(54) ADJUSTABLE RESISTANCE JOINT BRACE

(76) Inventor: Phong Tran, Tarzana, CA (US)

( * ) Notice: Subject to any disclaimer, the term of this patent is extended or adjusted under 35 U.S.C. 154(b) by 170 days.

(21) Appl. No.: 12/814,400

(22) Filed: Jun. 11, 2010

(65) Prior Publication Data

US 2011/0306911 A1   Dec. 15, 2011

(51) Int. Cl.
*A61F 5/00* (2006.01)

(52) U.S. Cl.
USPC .................. 602/16; 602/20; 602/26

(58) Field of Classification Search
USPC .......... 602/16, 12, 20–21, 23–27; 403/92, 94, 403/96–97; 16/239–241, 336–341; 482/114, 115, 118
See application file for complete search history.

(56) References Cited

U.S. PATENT DOCUMENTS

| | | | |
|---|---|---|---|
| 2,832,334 A * | 4/1958 | Whitelaw | 601/33 |
| 4,524,764 A * | 6/1985 | Miller et al. | 602/16 |
| 4,718,665 A | 1/1988 | Airy et al. | |
| 4,938,206 A | 7/1990 | Harris et al. | |
| 5,036,837 A | 8/1991 | Mitchell et al. | |
| 5,052,379 A | 10/1991 | Airy et al. | |
| 5,074,290 A | 12/1991 | Harris et al. | |
| 5,154,382 A * | 10/1992 | Hoshino | 248/185.1 |
| 5,358,469 A * | 10/1994 | Patchel et al. | 602/5 |
| 5,395,304 A | 3/1995 | Tarr et al. | |
| 5,415,508 A * | 5/1995 | Pleva | 411/11 |
| 5,624,386 A | 4/1997 | Tailor et al. | |
| 5,658,241 A | 8/1997 | Deharde et al. | |
| 5,749,840 A * | 5/1998 | Mitchell et al. | 602/5 |
| 5,860,943 A * | 1/1999 | Bloedau et al. | 602/16 |
| 5,873,847 A * | 2/1999 | Bennett et al. | 602/16 |
| 6,039,709 A * | 3/2000 | Bzoch | 602/26 |
| 6,129,690 A | 10/2000 | Hamlin et al. | |
| 6,471,664 B1 | 10/2002 | Campbell et al. | |
| 6,872,187 B1 | 3/2005 | Stark et al. | |
| 7,207,960 B2 * | 4/2007 | Kenney | 602/5 |
| 7,517,330 B2 * | 4/2009 | Deharde et al. | 602/16 |
| 7,534,220 B2 | 5/2009 | Cormier et al. | |
| 2004/0049291 A1 | 3/2004 | Deharde et al. | |
| 2005/0177082 A1 * | 8/2005 | Bledsoe | 602/26 |
| 2005/0209541 A1 | 9/2005 | Kenney | |
| 2006/0106328 A1 | 5/2006 | Sieller et al. | |
| 2008/0097269 A1 | 4/2008 | Weinberg et al. | |
| 2008/0195013 A1 | 8/2008 | Ingimundarson et al. | |
| 2009/0227926 A1 | 9/2009 | Cormier et al. | |

OTHER PUBLICATIONS

International Search Report and Written Opinion with Search History for International Application No. PCT/US11/40073; Search and Opinion completed Oct. 4, 2011; date of mailing Oct. 13, 2011; 10 pages.

* cited by examiner

*Primary Examiner* — Patricia Bianco
*Assistant Examiner* — Kari Petrik (57) ABSTRACT

An adjustable resistance joint brace with a pair of pivotally interconnected semi-flexible struts compressing a rubber disc washer to impart resistance during knee, elbow, ankle and hip flexion and extension. A manually adjustable knob controls the amount of resistance by squeezing together the upper strut, a rubber disc washer in between, and the lower strut. The brace includes a sleeve for housing the struts and the brace opposes movements when the struts articulate about a transverse axis corresponding to the anatomical pivot axis of the body joint of the knee, elbow, ankle, and hip. At the pivot axis, a turn of the knob clockwise tightens the brace and a counterclockwise turn of the knob would lessen the resistance. The brace has application for dynamic sports movements, daily routine movements, rehabilitation and weightlessness strength training.

19 Claims, 8 Drawing Sheets

ADJUSTABLE RESISTANCE JOINT BRACE

FIELD OF THE INVENTION

The present invention relates to ergonomic, sports, athletic knee and elbow braces, and more particularly to an exercising brace including an adjustable resistance control, semi-rigid frame, compressible washer and ventilated components.

BACKGROUND OF THE INVENTION

In the field of knee and elbow braces or supports, it is desirable that the brace include arrangements for resisting the movements of flexion and extension at the joint of the knee and the elbow. Various knee brace arrangements have been proposed, and these have included upper struts for extending along the thigh, and lower struts for extending along the lower leg or calf. These are normally provided both on the inside (medial) to the leg and on the outer (lateral) side of the leg; and these struts are usually padded and held in place with straps. The upper and lower struts are coupled together so that they could pivot during flexion and extension of the knee, elbow, ankle, and hip.

Strengthening of the joints, such as the knee, elbow, ankle and hip can employ various approaches. In one approach, an elastic band is attached to each leg at the ankle and resistance is applied with movement. The elbows are similarly strengthened by attaching a resistance band from each wrist to a hip strap. Resistance is applied when the arms move.

In another approach, portable weights are strapped at the ankle and wrist to provide a constant weighted resistance to the limbs. These sports devices are widespread and their relatively low cost, availability and simplicity have contributed to their usefulness.

The most effective tools for strengthening the muscles around the knee, elbow, ankle, and hip joints are exercise machines, such as leg extension, prone leg curl, arm extension, preacher curl, calf raise and glute machines. These machines are generally found in physical therapy, athletic training, health and wellness and research facilities. They provide high resistive closed chain forces, while providing a unique tailoring of the strengthening regime to nearly any individual. Their broad abilities increase their proficiency as a strengthening tool.

The prior art braces have some usefulness, although they still remain bulky and heavy and inefficient for strengthening everything (muscles, tendons, ligaments and meniscus) around the joints. Consequently, a need exists for an improved adjustable resistance joint brace.

SUMMARY OF THE INVENTION

An objective of this invention is to provide a brace for the joints (knee, elbow, ankle, wrist, and hip) that is light, easy to use, and has one and/or several points of resistant adjustments and is ergonomically configured.

The present invention is an adjustable resistance joint brace and its components for use therewith. In an exemplary embodiment of the present joint brace, the adjustable resistance joint brace construction operates superior of the pivot arrangements so that incremental resistance is maximized by turning a superior face plate on the brace. With this simplified ergonomic construction, the adjustable resistance joint brace adjustments may easily be manipulated while the brace is mounted on the leg. Turning of the superior face plate clockwise relative to the brace axis point increases the compression of the upper and lower struts onto a washer in between them. This would in turn result in an increase in resistance in flexion and extension at the joint.

In order to achieve the foregoing results in one illustrative embodiment, the pivoting assembly interconnecting the upper and lower struts includes, for both extension and flexion, a clamping device to hold the assembly together while resistance could be modified. The clamp would include an inferior circular or arcuate catch plate on the bottom and a superior disc with recesses facing or opening up at the top. A mounted nut assembly aligns and holds everything together inside the clamp while the control knob binds everything together and varies the resistance.

Viewed from a different aspect, the pivoting assembly may include an outer cover or closure plate which is part of the control knob. The control knob sits on an upper disc of the clamp which in turn sits on the first strut, then a washer, then the second strut, then a base disc, and finally a cushion pad. This assembly is held together by a screw which runs through all the layers except the cushion pad.

The construction of this exercise device exemplifies a relatively thin overall configuration of the pivoting assembly, which may be only about one-half inch thick at the axis and about 1.5 cm thick at the strut. Furthermore, to provide adequate strength and compactness, the struts and its components are preferably, but not limited to, made of high strength material such as steel, titanium, zinc alloys, aluminum, fiberglass, or other high strength metals or high strength plastic or polymers.

The construction of the brace includes sleeves to support the strut frame and the sleeve is preferably constructed of a breathable, yet sturdy, resilient elastic material like neoprene. Each strut, all upper, lower, lateral and medial, is positioned in its own pocket on the sleeve of the brace and further held in place by straps on the sleeve that interlace the struts and are fastened with Velcro®.

As mentioned above, one strut extends from the pivot assembly up the upper limb or body, and the other strut extends from the pivot down the lower limb or body. The pivot assembly is mounted right next to the point of axis of a joint and is braced up against the joint via a cushion pad.

Additional aspects of the brace may include the face plate, which is mounted on the outermost surface of the pivot assembly for adjusting the amount of resistance during flexion and extension, could be numbered in a clockwise manner to indicate the levels of resistance. The numbers are marked along the peripheral portion of the face plate. An upper disc of a clamp (immediately under the control knob) has an indicating arrow which targets the desired number for the desired resistance. Thus, the same level of resistance could be duplicated on another brace of a different body part.

Alternatively, the face plate could be color coded in a clockwise manner to indicate the levels of resistance. The colors could be presented in a pie chart fashion covering the entire face plate. The upper disc of the clamp has an indicating arrow which targets the desired color for the desired resistance. Thus, the same level of resistance could be duplicated on another brace of a different body part. The face plate could be interchangeable to permit variation of designs.

The present invention contemplates several levels of resistance joint braces. Some joint braces will be designed with a higher level of resistance to start and progressively get harder, while other joint braces will start out with no resistance and gradually get harder. The control knob would rotate about 360 degrees. A small stopper rod is attached to the side of the control knob that will stop the rotation of the control knob when it hits the stopper rod on top of the clamp.

DESCRIPTION OF THE DRAWINGS

The aforementioned object and advantages of the present invention will be more fully understood hereinafter as a result of consideration of a detailed description of the invention when taken in conjunction with the accompanying drawings in which.

DETAILED DESCRIPTION OF THE DRAWINGS

Figure 1:
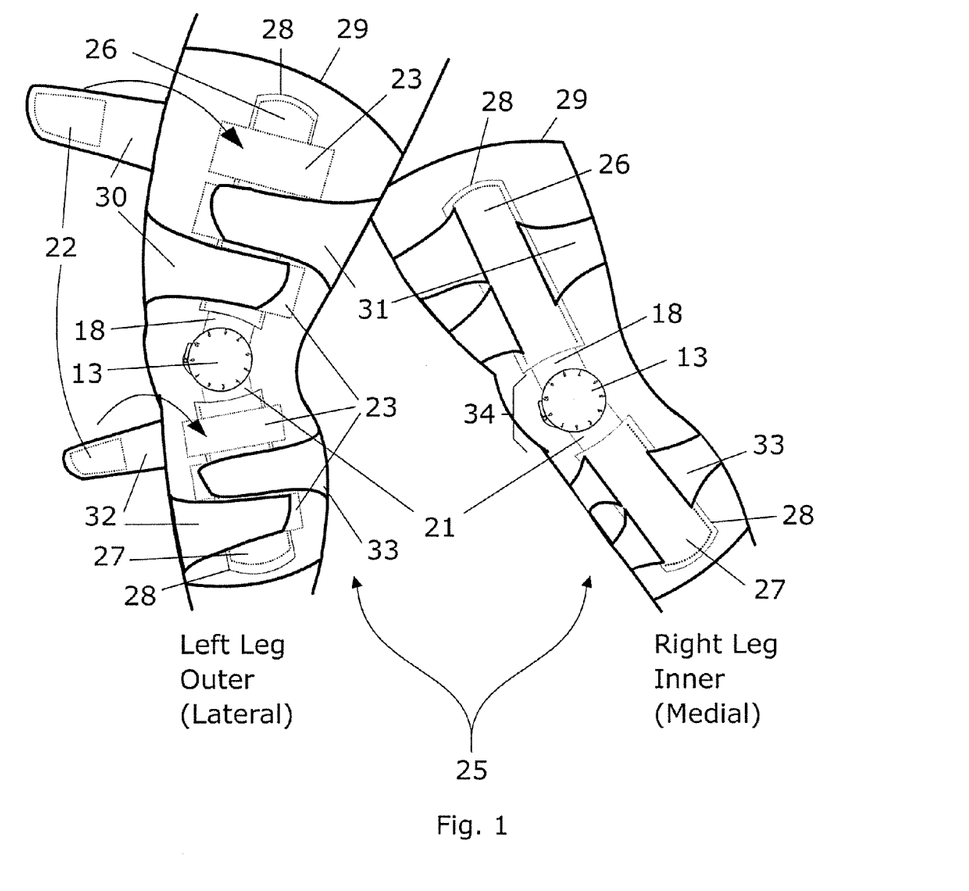
FIG. 1 is a perspective view of the joint brace assembly (i.e. a knee brace) of the present invention.
Figure 2:
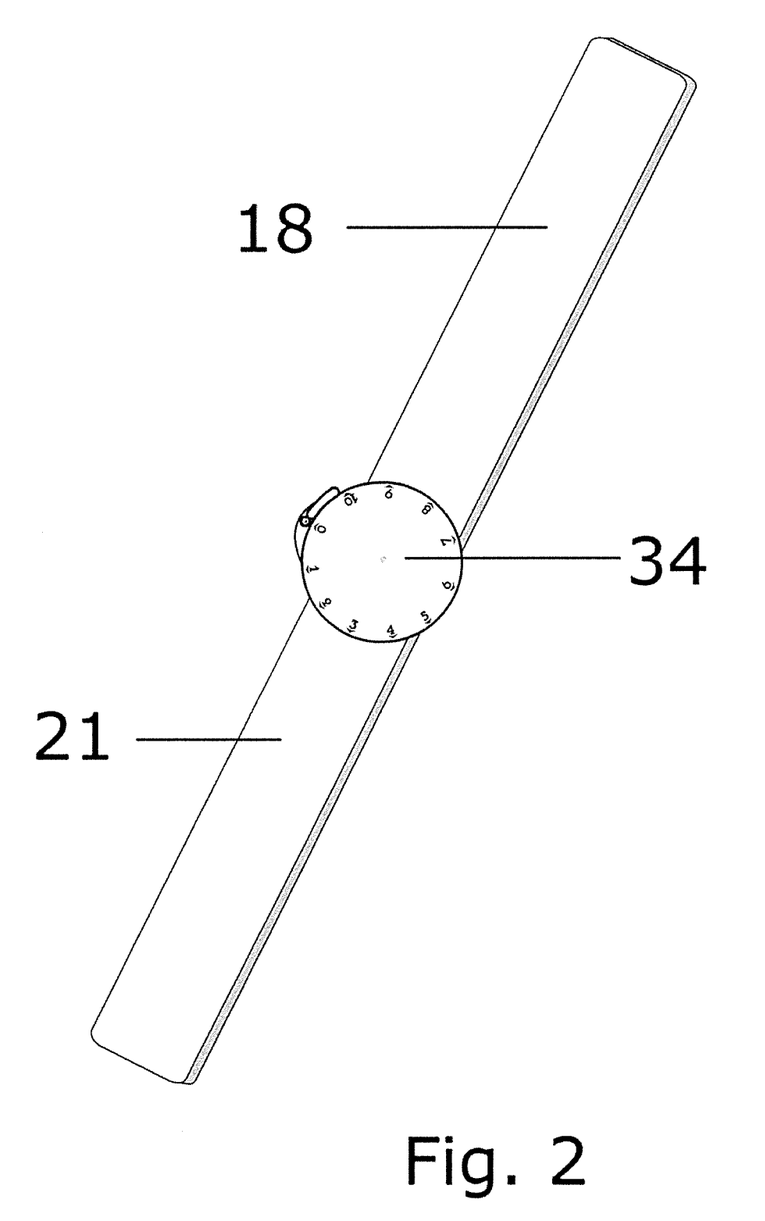
FIG. 2 is a plan view of the adjustable resistance pivot system shown in the knee brace assembly of FIG. 1.

Referring to the drawings, FIGS. 1 and 2 show two leg braces 25 for the knees, each including two struts 18 and 21; strut 18 extending up and strut 21 extending down the leg from a central adjustable resistance pivot assembly 34. Each brace has struts 18 and 21 and assembly 34 positioned on either side of the knee. Each brace includes a sleeve 29 which fits around the extremity of the user, in this case the leg. Each sleeve 29 has four pockets 28 for the struts to fit into and two are stitched to the outside (laterally) upper leg portion 26 and lower leg portion 27, and two are stitched to the inside (medially) upper leg portion 26 and lower leg portion 27. Extending from the adjustable resistance pivot assembly 34 along the outer (lateral) upper leg portion 26 in the upper pocket is strut 18, and extending down the outer (lateral) lower leg portion 27 in the lower pocket is strut 21. Because of their location on the side of the knee joints, the entire adjustable resistance pivot system (two struts and the adjustable resistance pivot assembly 34) on the lateral left leg is the same as that of the entire adjustable resistance pivot system of the medial right side. And inversely, the entire adjustable resistance pivot system of the lateral right leg (not shown) is the same as that of the medial left leg (not shown), and thus, are interchangeable.

For a knee brace, struts 18 are sometimes referred to as femoral struts (as extending along the femur or the principal upper leg bone) and struts 21 are referred to as tibial struts (extending along the tibia and fibula, or the principal lower leg bones). For an elbow brace, these struts are sometimes referred to as humeral struts (as extending along the humerus or the principal upper arm bone) and forearm struts (as extending along the forearm bones, the principal ulna and radius bones). For an ankle brace, these struts are sometimes referred to as ankle struts (as extending along the lower tibia and fibula, or the principal lower leg bones and foot struts (extending along the foot, or the principal foot bones). For a hip brace, these struts are sometimes referred to as hip struts (as extending along the hip, or the principal hip bones) and the femoral struts (as extending along the femur or the principal upper leg bone).

Once the struts are in the pockets 28, a series of straps 30 and 31 sewn on the upper leg portion 26 of sleeve 29, and a series of straps 32 and 33 sewn on the lower leg portion 27 of sleeve 29 are used to adjust the tightness of the sleeve on the leg of the user. These straps, when applied and attached to their respective VELCRO® counterparts 22 and 23, will add more stability to the struts in the pockets.

Figure 3:
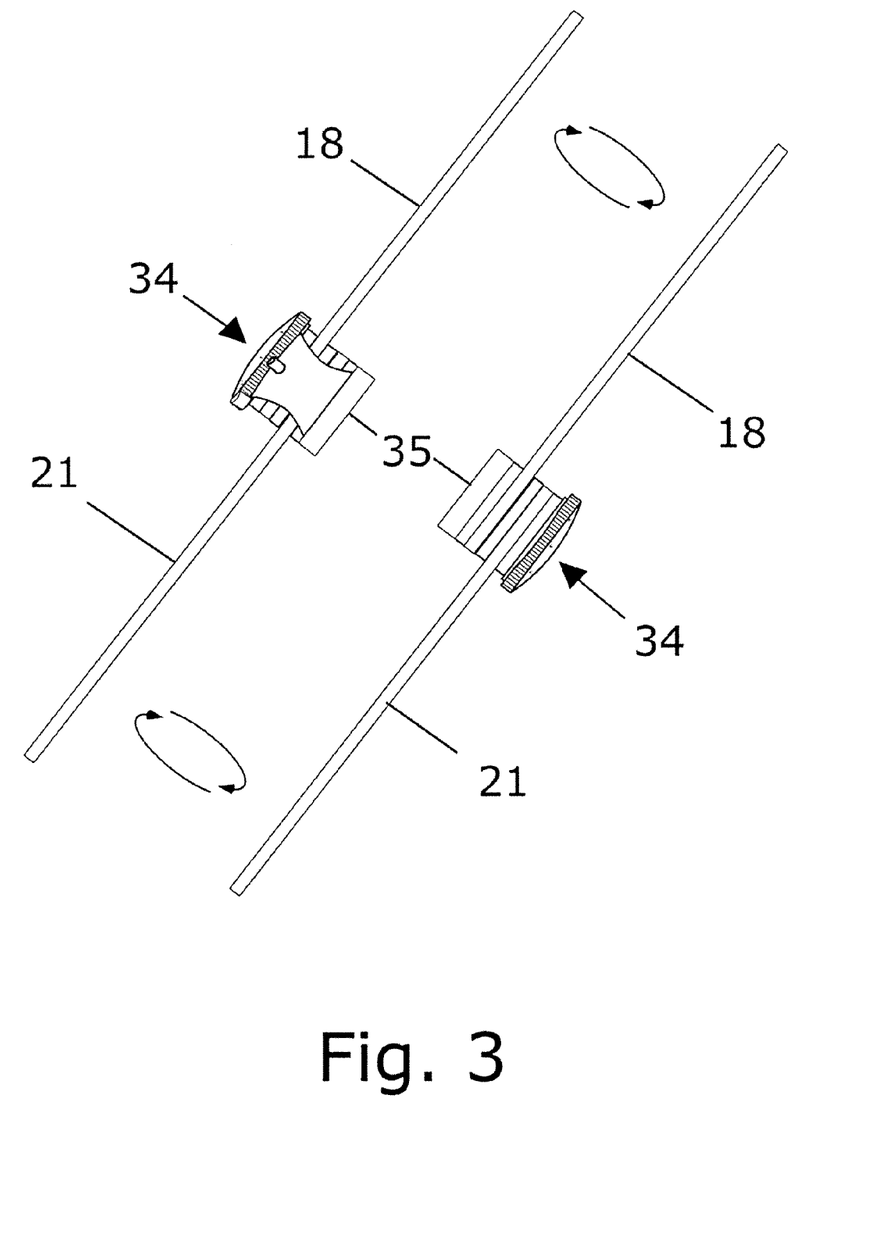
FIG. 3 is a side plan view of the adjustable resistance pivot system of FIG. 2 and a back view of it turned 180 degrees along the vertical axis of the upper and lower struts.
Figure 4:
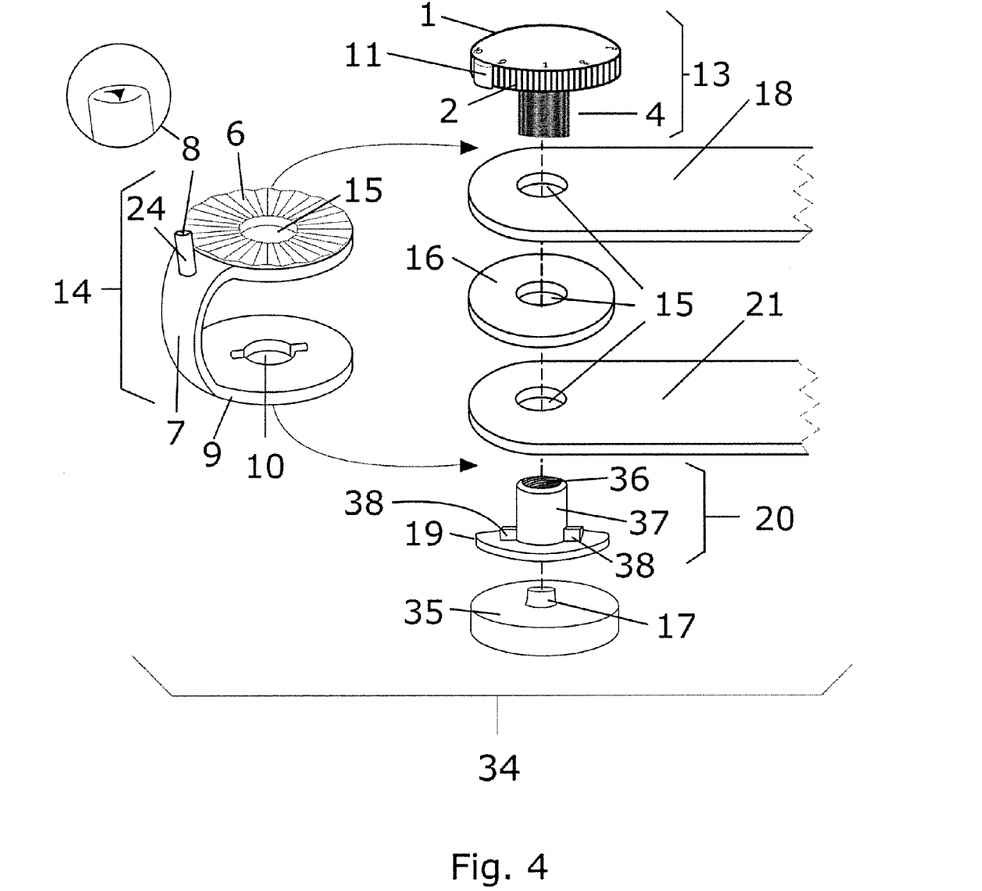
FIG. 4 is an exploded enlarged perspective detail view of the adjustable resistance pivot system of FIG. 1.

Bracing the adjustable resistance pivot assembly 34 at the axis of rotation of the joint is a circular padded cushion 35 as seen in FIGS. 3 and 4. This circular padded cushion 35, which underlies the adjustable resistance pivot assembly 34, cushions the force of the adjustable resistance pivot assembly 34 onto the sides, lateral and medial, of the knee. The cushion 35 has a positioning protrusion 17 for alignment with the assembly 34. The entire knee brace assembly is held together in this manner for active usage conditions.

The sleeve 29 is composed of a breathable neoprene or neoprene like material that would allow for a little stretching. The assembly of this pliable sleeve is simple and straight forward to allow faster and more efficient production. A pre-measured neoprene sheet is stitched together at the ends to make a hollow cylinder that is the main body of the sleeve. It is now similar to an arm sleeve of a shirt. Then it is laid sideway and pressed flat with the new stitching at one end. Premade strut pockets 28, upper and lower are then aligned to be exactly in the middle of this flattened sleeve. Having an adjustable resistance pivot assembly 34 adjacent the pockets will help guide the placement of the pockets onto the neoprene sleeve. Once the pockets are in their right places, they are stitched permanently onto the neoprene sleeve. This is repeated onto the other side of the brace 25 so that one brace will have pockets to hold two sets of the adjustable resistance joint assembly 34 and struts 18 and 21.

The pockets 28 are composed of a non-stretchy silk-like material that will not expand with the usage of the struts in flexion and extension about a pivotal assembly. Pockets 28 on the lateral or outer side of the brace are made by placing two rectangular, non-stretchy, silk-like material sheets, one on top of the other. With a predetermined measured length, the two sheets are stitched together with strong threads. To create a pocket, two long sides and one short side are 'crossed-stitched' while leaving the other short side alone to create an opening for the strut to fit into. The stitching of the two rectangular sheets together is done along the perimeter of the three sides. There is a border extended from the three stitched sides that is about ½ inch long. This stitched border will later be stitched to the neoprene sleeve to secure the pockets onto the sleeve. Next, a Velcro® sheet (the same size as the two sheets used earlier for pockets 28) with loops facing upward, is placed on top of the already stitched pocket. Now, the stitching pattern (crossed-stitched) that was done earlier around the perimeter of the two sheets to create the pocket with border is repeated again. This not only secures the Velcro® sheet (with the loops facing upward) to the pocket, it further reinforced the stitching of the pocket's perimeter to better hold the struts inside of it.

Pockets 28 on the medial or inside of the brace are constructed in the same fashion as the lateral pockets with two rectangular sheets crossed-stitched together around a predetermined perimeter of three sides while leaving one short side unstitched to create an opening of a pocket for the struts to fit into. However, medial pockets differ from lateral pockets with the addition of a third layer. Medial pockets will have three neoprene straps stitched onto the already stitched pocket. Relative to the pocket, two straps will be extended perpendicularly from one side of the pocket and the other strap will extend perpendicularly from the other side of the pocket. The three straps are staggered to each other in that one extends to the left, the next to the right and the last to the left. At the end of each strap, there is a Velcro® sheet 22 with the hooks facing inward) crossed-stitched to the strap. These three staggered straps will wrap around a body part, like a thigh, and anchor onto the exposed Velcro® loops 23 of the outer pockets. Two straps 30 would wrap around the thigh in one direction while the third strap 31 wraps around in the opposite direction. This would ensure a firm grip of the sleeve to the thigh or any other body parts. The same construction of pockets and straps would apply for upper leg portion 26 and the lower leg portion 27.

The illustration of FIG. 1 is of the outside (lateral) of the left leg and the inside (medial) of the right leg. On the inside of the left leg (not shown) and the outside of the right leg (not shown) are similar assemblies to those shown in FIG. 1, with two adjustable resistance pivot assemblies. These four units are similar and are held to the legs by the straps 30, 31, 32 and 33. Most of the components of the inner assembly are common to the outer assemblies, especially with the struts and the adjustable resistance pivot assemblies being mirror images of one another.

FIG. 3 is a side plan view of the assembly of FIG. 2. The adjustable resistance pivot assembly 34 will be described in greater detail herein below.

To better understand the operation of the adjustable resistance pivot assembly, it is useful to refer to the exploded view of FIG. 4. In operation, the two struts 18 and 21 are pivoted relative to one another while compressing a center washer 16 about a cylindrical mounted nut 20. A plastic (two discs) clamp 14 secures the two struts 18 and 21 to washer 16 (strut 18 on top of washer 16 and strut 21 on the bottom of washer 16) and provide a stable anti-slip platform for the control knob 13 to adjust the desire resistance settings. At the top of the clamp 14 is an arrow 8 pointing toward the control knob 13 to indicate which level of resistance that adjustable resistance pivot system 34 is currently on. Turning the control knob 13 clockwise will: increase the numbers on the control knob 13; increase the compression of the clamp 14 onto the two struts 18 and 21; increase the compression of the two struts 18 and 21 against a center washer 16 which will increase the overall torsional resistance of flexion and extension at the joint in which the brace is attached.

Figure 5:
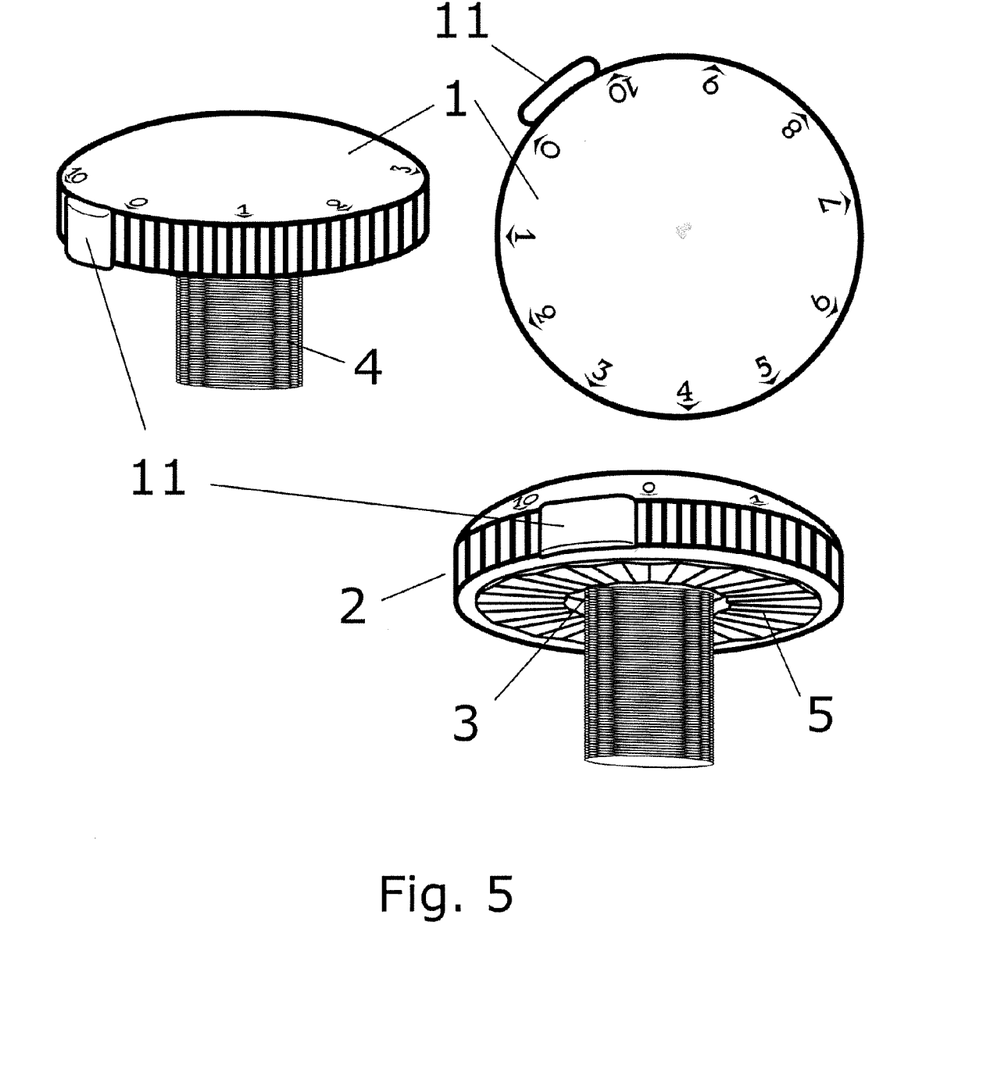
FIG. 5 illustrates three different enlarged plan and perspective views of a control knob (screw) for the adjustable resistance pivot system of FIG. 4.

The arrow indicia 8 points toward a cover plate 1 of the control knob 13. As seen in FIG. 5, visible on the cover plate 1 (of the control knob 13) are degree indicia which may be read by the arrow 8 on the upper washer 6 (of the clamp 14). To change the amount of resistance of motion, the control knob 13, which starts at the lowest resistance level of 0 (zero), is dialed to the right to the desired resistance setting. Incidentally, the outermost perimeter 2 of the control knob 13 are ribbed or textured for non-slip engagement.

Concerning the different resistance settings, when the control knob 13 is at 0 (zero resistance) the user is free to fully move in both flexion and extension without resistance. As the control knob 13 is turned clockwise, the numbers on the cover plate 1 increase at the arrow indicia 8. This corresponds to an increase in resistance for joint flexion and extension. The higher the number at the arrow indicia 8, the greater the resistance will be.

Incidentally, the control knob 13 represents the head of the screw that extends all the way through the adjustable resistance assembly 34. Therefore, since every support members is housed in between the control knob 13 and its receiving end, the mounted nut 20, when the control knob 13 tightens clockwise, compresses all the support members in between them together. The more the control knob 13 turns clockwise, the greater the compression and the greater the resistance of the two struts 18 and 21 moving about the washer 16 and the clamp 14.

As mentioned above, the control knob 13 represents the head of the screw with the cylindrical right-hand thread portion (also known as the shank 4) on the underside of the head to the tip that extends all the way through the adjustable resistance pivot assembly 34. The underbelly 5 of the control knob 13 has a series of valleys radiating outward from the center which receive the same series of valleys radiating outward from the center of the upper disc 6 of the clamp 14 as described below.

Figure 7:
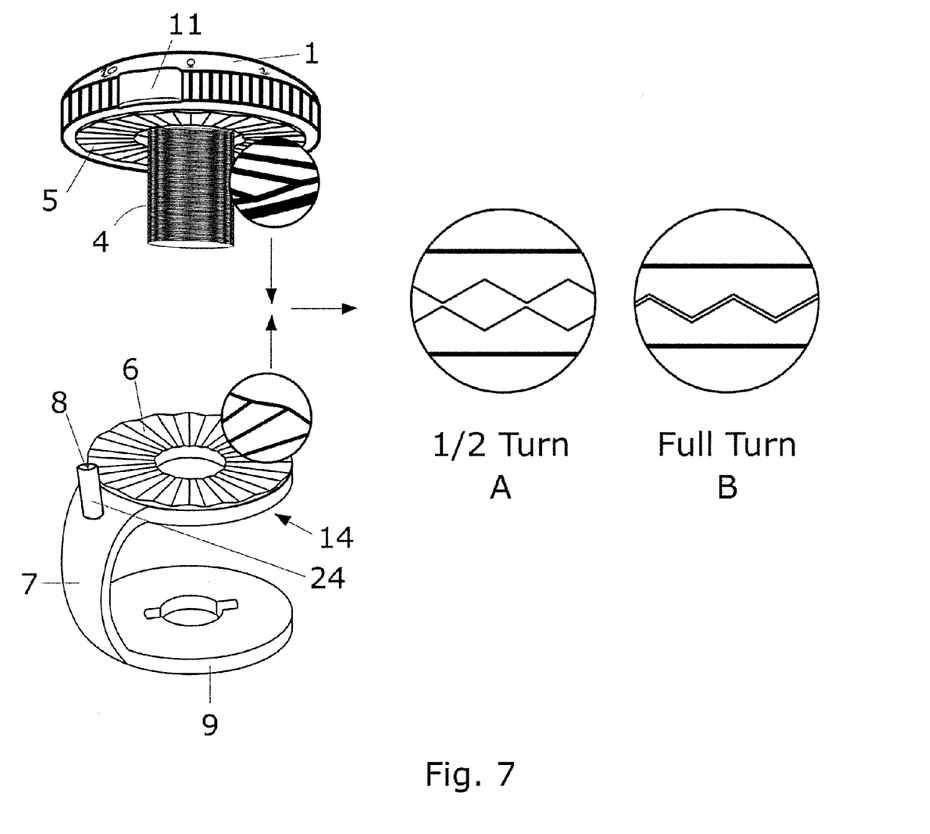
FIG. 7 is an enlarged perspective view of the control knob and the clamp of FIG. 4 illustrating their points of contact during rotation.

FIG. 5 displays the underbelly 5 with a series of valleys protruding downward and FIG. 4 displays the top disc 6 with a series of valleys protruding upward. FIG. 7 best displays the relationship between the underbelly 5 and the top disc 6. When the control knob 13 is screwed about half way into its mounted nut 20, the underbelly 5 will make contact with upper washer 6. Their series of valleys will interconnect with one another to form an interlocking mechanism. When turning the control knob 13 either clockwise or counterclockwise, the series of valleys of the underbelly 5 will simply go up and over the series of valleys of disc 6 and then down and lock again. With every half turn of the control knob 13, the top disc 6 will be pushed downward as the peak of the series of valleys of the underbelly 5 go over the peaks of the series of valleys of disc 6. Then the disc 6 returns back up to fit perfectly into the underbelly 5 at full turn. This spring-like property is made possible by the arch back 7 of the clamp 14. The arch back 7 connects the upper disc 6 and lower disc 9 with a slight curve to give the clamp 14 its spring-like quality.

Referring again to FIG. 4, clamp 14, which encompasses the upper strut 18, washer 16 and the lower strut 21, is also held together by mounted nut 20 that extends all the way up through them. Once the bottom disc 9 of the clamp 14 is placed over the mounted nut 20, the opening 10 (of the bottom disc 9) with its two rectangular pieces cut-out spaced 180 degrees from each other, will fit perfectly on top of the mounted nut 20 with the two cube-like protrusions 38. These cubes 38 are positioned 180 degrees from each other and fixed to a bottom disc 19 and the threaded sleeve 37. This will hold the clamp 14 and the mounted nut 20 in one place and anchor the assembly when the control knob 13 turns clockwise to tighten the resistance or counterclockwise to loosen the resistance. While in between the upper disc 6 and the lower disc 9 of the clamp 14, the combined height measurement of the upper strut 18, washer 16 and the lower strut 21 will be about a centimeter shorter than the height measurement of the clamp 14. This is necessary because the arch 7 of the clamp 14 is flexible and can bend inward to compress the inner components when acted upon by the control knob 13.

Referring again to FIG. 7, upper disc 6 of clamp 14 is perforated with a series of valleys stemming from the center outward. There is a hole 15 in the center of disc 6 to accommodate the threaded sleeve 37 of the mounted nut 20 which protrudes up to the top of disc 6 in order to receive the shank 4 and help stabilize the structure of the clamp 14. Arch 7 connects the upper disc 6 to the lower base disc 9 with a slight crescent to allow bending. A stop bar 24 is attached under to the indicia arrow 8 to arrest the stop strip 11 which is attached to the control knob 13 to prevent the knob from rotating more than 360 degrees.

FIG. 5 shows an enlarged perspective view to the control knob 13 where upon there is an inner circular cut-a-way 3 surrounding the shank 4 in order to accommodate the thickness of the threaded sleeve 37 of the mounted nut 20. This indentation 3 into the underbelly 5 is only approximately one centimeter measured from the shank outward and does not affect the effectiveness of the series of valleys interconnecting with the series of valleys of disc 6.

The flat washer 16 in FIG. 4 is a semi-rigid disc used to promote resistance upon which the two struts 18 and 21 compress, and it also serve the function of a spacer in facilitating rotation of the overlying parts. It may be formed from plastic such as nylon, rubber, be a spring coil or other high resistance material.

Figure 6:
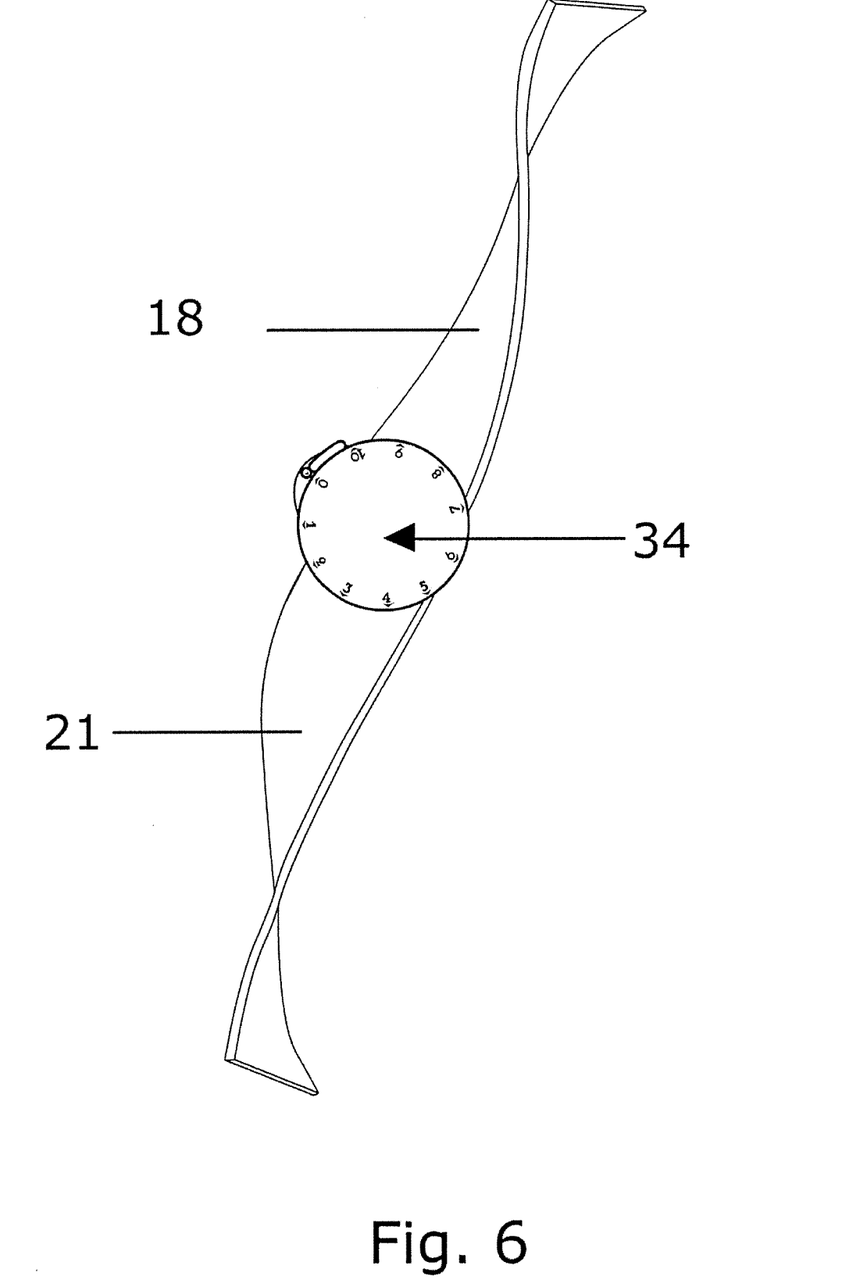
FIG. 6 is a perspective view of the struts of FIG. 1 illustrating the ability to twist or rotate.

Each strut 18 and 21 will fit into their respective strut pockets 28. The strut pockets 28 can also be made from a canvas like material having a generally rectangular cross-section with a rectangular channel extending from the center. The rectangular channel of the strut pockets 28 is designed to slidably receive respective struts 18 and 21. Each strut is preferably made from a semi-rigid material such as plastic, fiber glass, wood, metal, aluminum or any composite that is high strength with a little flexibility as shown in FIG. 6. The preferred elongated flat plate shape of the struts 18 and 21 allows the struts to slightly twist but not side bend along the thin outer perimeter. The twisting ability of the struts is crucial when applied to the limbs because movements of the limbs occur in multiple planes whereas the limbs not only flex and extend but also rotate and twist. Struts 18 and 21 accommodate the limbs natural multi-planar movements by twisting and bending with the users' natural flow of multi-planar, multi-facet joints movements.

For the shank 4 of control knob 13, although there are many systems (British Standard Whitworth, British Association-BA system and the Unified Thread Standard) for specifying the dimensions or screws, the ISO metric screw thread preferred series is specified. Its basic principles are defined in the International Standard ISO 262 for the smaller subset of diameter and pitch for screws, nuts and bolts. ISO metric screw threads are designated by the letter M followed by the major diameter of the thread in millimeters (e.g., M8). For variety, the thread of shank 4 could be the normal coarse pitch (e.g., 1.25 mm in the case of M8) for one knee brace 25, it could be also be smaller where its pitch in millimeters is appended with a multiplication sign (e.g. M8×2) for another. The latter dimension shows that the thread of shank 4 has an outer diameter of 8 mm and advances by 2 mm per 360° rotation. The diameters of shank 4 will vary depending on the desired resistance needed for the different types and levels of joints brace.

The mounted nut 20 has a tapped hole 36. Since the nominal diameter of the metric screw is the outer diameter of the thread (of shank 4), the tapped hole 36 has an internal diameter of the size of the screw minus the pitch of the thread. Thus, for an M8 control knob (screw) 13, which has a pitch of 1 mm, is made by threading an 8 mm shank and the threaded hole 36 is made by tapping threads in a hole somewhat smaller than 8 mm.

Figure 8:
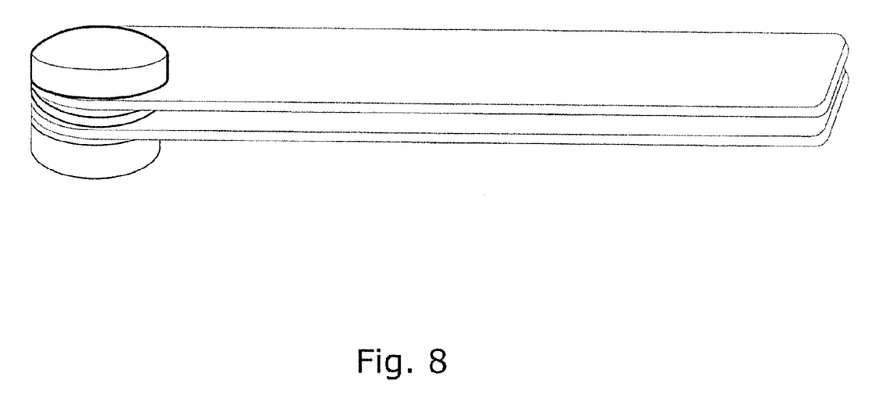
FIG. 8 is a perspective view of an alternative resistance pivot system where a rivet (with predetermined resistance) holds the entire resistance pivot system together.

Although it is preferable to have the ability to adjust the resistance of the brace, FIG. 8 illustrates an alternative resistance pivot assembly 40 for struts 18 and 21 which has a predetermined resistance by having a designated rivet 41 which holds the entire resistance pivot assembly together. In this embodiment a single resistance level is identified for use by the user.

Although the present invention has been described and illustrated with respect to various embodiments thereof, it is to be understood that the invention is not to be so limited since changes and modifications can be made herein which are within the full intended scope of the invention as hereinafter claimed.

What is claimed is:

1. An adjustable resistance joint brace comprising:
   a first strut having a top surface, a bottom surface, and an aperture extending through the top surface and the bottom surface;
   a second strut having a top surface, a bottom surface, and an aperture extending through the top surface and the bottom surface;
   a central adjustable resistance pivot assembly joining an end of the first strut with an end of the second strut, the central adjustable resistance pivot assembly comprising:
      a center washer positioned between the bottom surface of the first strut and the top surface of the second strut, wherein an opening in the center washer is aligned with the aperture of the first strut and the aperture of the second strut;
      a clamp comprising a first disc and a second disc for securing the first strut and the second strut to the center washer, each disc having a hole therein that is aligned with the hole of the other disc, the apertures of the first and second struts, and the opening in the center washer;
      wherein the first disc of the clamp is positioned above the top surface of the first strut, and the second disc of the clamp is positioned below the bottom surface of the second strut;
      a mounting nut positioned below the second disc of the clamp and extending through the hole in the second disc of the clamp, the aperture of the second strut, and the center washer;
   a threaded control knob positioned on a top surface of the first disc of the clamp and extending through the central adjustable resistance pivot assembly for insertion into the mounting nut;
   wherein the threaded control knob interconnects with the top surface of the first disc of the clamp to control, upon rotation, compression of the first strut, the second strut, and the center washer, thereby controlling a resistance level during flexion and extension of the first strut and the second strut;
   a sleeve for positioning the brace; and
   pockets positioned on the sleeve for receipt of a portion of the struts extending away from the central adjustable resistance pivot assembly;
   wherein the clamp comprises a flexible arch connecting the first disc with the second disc, such that the flexible arch is formed to bend inward when acted upon by the threaded control knob.

2. The brace of claim 1, wherein the clamp includes a stop bar and indicator indicia.

3. The brace of claim 1, wherein the threaded control knob has resistance setting indicia positioned on a cover plate.

4. The brace of claim 1, wherein the central adjustable resistance pivot assembly further comprises a cushion adjacent the mounting nut.

5. The brace of claim 1, wherein the sleeve has a plurality of straps for adjusting a fit of the sleeve.

6. The brace of claim 1, wherein the sleeve comprises a lateral side and a medial side, and wherein the first strut, the second strut, and the central adjustable resistance pivot assembly are positioned on each of the lateral and medial sides of the sleeve.

7. The brace of claim 1, wherein the sleeve comprises a stretchable material.

8. The brace of claim 1, wherein the second disc of the clamp comprises at least one cut-out, and the mounting nut comprises at least one protrusion, wherein the at least one protrusion is insertable into the at least one cut-out to anchor the central adjustable resistance pivot assembly during rotation of the threaded control knob.

9. A joint brace comprising:
   a first strut having a top surface, a bottom surface, and an aperture extending through the top surface and the bottom surface;
   a second strut having a top surface, a bottom surface, and an aperture extending through the top surface and the bottom surface;
   a central adjustable resistance assembly pivot joining an end of the first strut with an end of the second strut, the central adjustable resistance pivot assembly comprising:
      a center washer positioned between the bottom surface of the first strut and the top surface of the second strut, wherein an opening in the center washer is aligned with the aperture of the first strut and the aperture of the second strut;
      a clamp comprising a first disc and a second disc for securing the first strut and the second strut to the center washer;
      wherein the first disc of the clamp is positioned above the top surface of the first strut, and the second disc of the clamp is positioned below the bottom surface of the second strut;
      a mounting nut positioned below the second disc of the clamp and extending through the hole in the second disc of the clamp, the aperture of the second strut, and the center washer;
   a threaded control knob positioned on a top surface of the first disc of the clamp and extending through the central adjustable resistance pivot assembly for insertion into the mounting nut;
   wherein the first strut, the second strut, and the central adjustable resistance pivot assembly are secured to a sleeve; and
   wherein the top surface of the first disc of the clamp comprises a series of valleys protruding upward, and a bottom surface of the threaded control knob comprises a series of valleys protruding downward, such that the top surface of the first disc of the clamp and the bottom surface of the threaded control knob interconnect with one another, such that rotation of the threaded control knob increases compression of the clamp and maintains a uniform and constant level of resistance of the central adjustable resistance pivot assembly during extension or flexion of the first strut and the second strut;
   wherein the clamp comprises a flexible arch connecting the first disc with the second disc, such that the flexible arch is formed to bend inward when acted upon by the threaded control knob.

10. The brace of claim 9, wherein the sleeve has separate pockets for receipt of at least a portion of the first strut and at least a portion of the second strut.

11. The brace of claim 9, wherein the clamp comprises a stop bar and indicator indicia.

12. The brace of claim 9, wherein the threaded control knob has resistance setting indicia positioned on a cover plate.

13. The brace of claim 9, wherein the central adjustable resistance pivot assembly further comprises a cushion adjacent the mounting nut.

14. The brace of claim 9, wherein the sleeve has a plurality of straps for adjusting fit of the brace.

15. The brace of claim 9, wherein the brace comprises a lateral side and a medial side, and wherein the first strut, the second strut, and the central adjustable resistance pivot assembly are positioned on each of the lateral and medial sides of the brace.

16. The brace of claim 9, wherein the sleeve comprises a stretchable material.

17. The brace of claim 9, wherein the second disc of the clamp comprises at least one cut-out, and the mounting nut comprises at least one protrusion, wherein the at least one protrusion is insertable into the at least one cut-out to anchor the central adjustable resistance pivot assembly during rotation of the threaded control knob.

18. An adjustable resistance joint brace comprising:
   a sleeve; and
   a pair of struts interconnected by a pivotal joint comprising a manually adjustable control knob, a compressible disc positioned between the pair of struts, and a clamp for securing the pair of struts and the compressible disc;
   wherein the manually adjustable control knob comprises a series of valleys protruding downward which interconnects with a series of valleys protruding upward from the clamp;
   wherein rotation of the manually adjustable control knob increases compression of the clamp about the pair of struts and the compressible disc, and maintains a constant resistance level on the pair of struts and the compressible disc during all points of pivot;
   wherein the clamp comprises an upper portion, a lower portion, and a flexible arch connecting the upper portion with the lower portion, such that the flexible arch is formed to bend inward when acted upon by the manually adjustable control knob.

19. The brace of claim 18, wherein the sleeve has pockets for receipt of at least a portion of each of the pair of struts extending away from the pivotal joint.

* * * * *